(12) United States Patent
Marcinek et al.

(10) Patent No.: US 8,126,527 B2
(45) Date of Patent: Feb. 28, 2012

(54) METHOD AND SYSTEM FOR DETERMINING THE CONTRIBUTION OF HEMOGLOBIN AND MYOGLOBIN TO IN VIVO OPTICAL SPECTRA

(75) Inventors: David J. Marcinek, Seattle, WA (US); Kevin Conley, Seattle, WA (US); Kenneth A. Schenkman, Seattle, WA (US)

(73) Assignee: University of Washington through its Center for Commercialization, Seattle, WA (US)

( * ) Notice: Subject to any disclaimer, the term of this patent is extended or adjusted under 35 U.S.C. 154(b) by 1516 days.

(21) Appl. No.: 11/462,283

(22) Filed: Aug. 3, 2006

(65) Prior Publication Data

US 2008/0033263 A1    Feb. 7, 2008

(51) Int. Cl.
*A61B 5/1455*    (2006.01)
(52) U.S. Cl. ......... 600/328; 600/322; 600/323; 600/326
(58) Field of Classification Search .................. 600/310, 600/322, 323, 328, 28; 356/364
See application file for complete search history.

(56) References Cited

U.S. PATENT DOCUMENTS

| | | | |
|---|---|---|---|
| 3,830,222 A | 8/1974 | Chance | 600/334 |
| 4,281,645 A | 8/1981 | Jobsis | 600/324 |
| 4,822,169 A * | 4/1989 | Distl et al. | 356/364 |
| 5,088,493 A | 2/1992 | Giannini et al. | 600/323 |
| 5,231,464 A | 7/1993 | Ichimura et al. | 600/310 |
| 5,284,137 A | 2/1994 | Kessler et al. | 600/317 |
| 5,879,294 A * | 3/1999 | Anderson et al. | 600/310 |
| 5,931,779 A | 8/1999 | Arakaki et al. | 600/310 |
| 6,505,059 B1 | 1/2003 | Kollias et al. | 600/316 |
| 7,113,814 B2 | 9/2006 | Ward et al. | 600/310 |
| 7,130,672 B2 | 10/2006 | Pewzner et al. | 600/324 |
| 7,313,424 B2 | 12/2007 | Mayevsky et al. | 600/310 |
| 2004/0111016 A1 | 6/2004 | Casscells et al. | 600/310 |
| 2005/0287548 A1 | 12/2005 | Bao et al. | 435/6 |
| 2007/0133984 A1 | 6/2007 | Maier et al. | 398/26 |

OTHER PUBLICATIONS

Matcher et al., Absolute quantification of deoxyhemoglobin concentration in tissue near infrared spectroscopy, Phys. Med. Biol. 39 (1994), 1295-1312.*
Arai et al., "Myocardial oxygenation in vivo: optical spectroscopy of cytoplasmic myoglobin and mitochondrial cytochromes", Feb. 22, 1999, pp. H683-H697.
Dupuis et al., "Up-regulation of mitochondrial uncoupling protein 3 reveals an early muscular metabolic defect in amyotrophic lateral sclerosis", Sep. 18, 2003, 19 pages.
Laiho et al., "Two-photon 3-D mapping of tissue endogenous fluorescence species based on fluorescence excitation and emission spectra", 2002, pp. 1064-1065.

(Continued)

*Primary Examiner* — Eric Winakur
*Assistant Examiner* — Chu Chuan (JJ) Liu

(57) ABSTRACT

This document discusses, among other things, quantification of hemoglobin content, and therefore blood volume, of muscle. An analysis of the optical spectra can determine the ratio of hemoglobin (Hb) to myoglobin (Mb) content in intact muscle. The peak position of the in vivo optical spectra from intact tissue is used to determine the ratio of Hb to Mb contributing to the optical signal. The wavelength of the peak is a linear function of the percent contribution of Hb to the optical spectra. Such analysis in combination with known Mb concentrations yields a non-invasive measure of the Hb content for in vivo muscle.

22 Claims, 6 Drawing Sheets

OTHER PUBLICATIONS

Marcinek et al., "Mitochondrial coupling in vivo in mouse skeletal muscle", Oct. 1, 2003, pp. C457-C463.

Marcinek et al., "Oxygen regulation and limitation to cellular respiration in mouse skeletal muscle in vivo", May 29, 2003, pp. H1900-H1908.

Schrauwen et al., "Oxidative Capacity, Lipotoxicity, and Mitochondrial Damage in Type 2 Diabetes", Jun. 2004, pp. 1412-1417.

Wallace, Douglas C., "A Mitochondrial Paradigm of Metabolic and Degenerative Diseases, Aging, and Cancer: A Dawn of Evolutionary Medicine", Jul. 12, 2005, pp. 359-407.

* cited by examiner

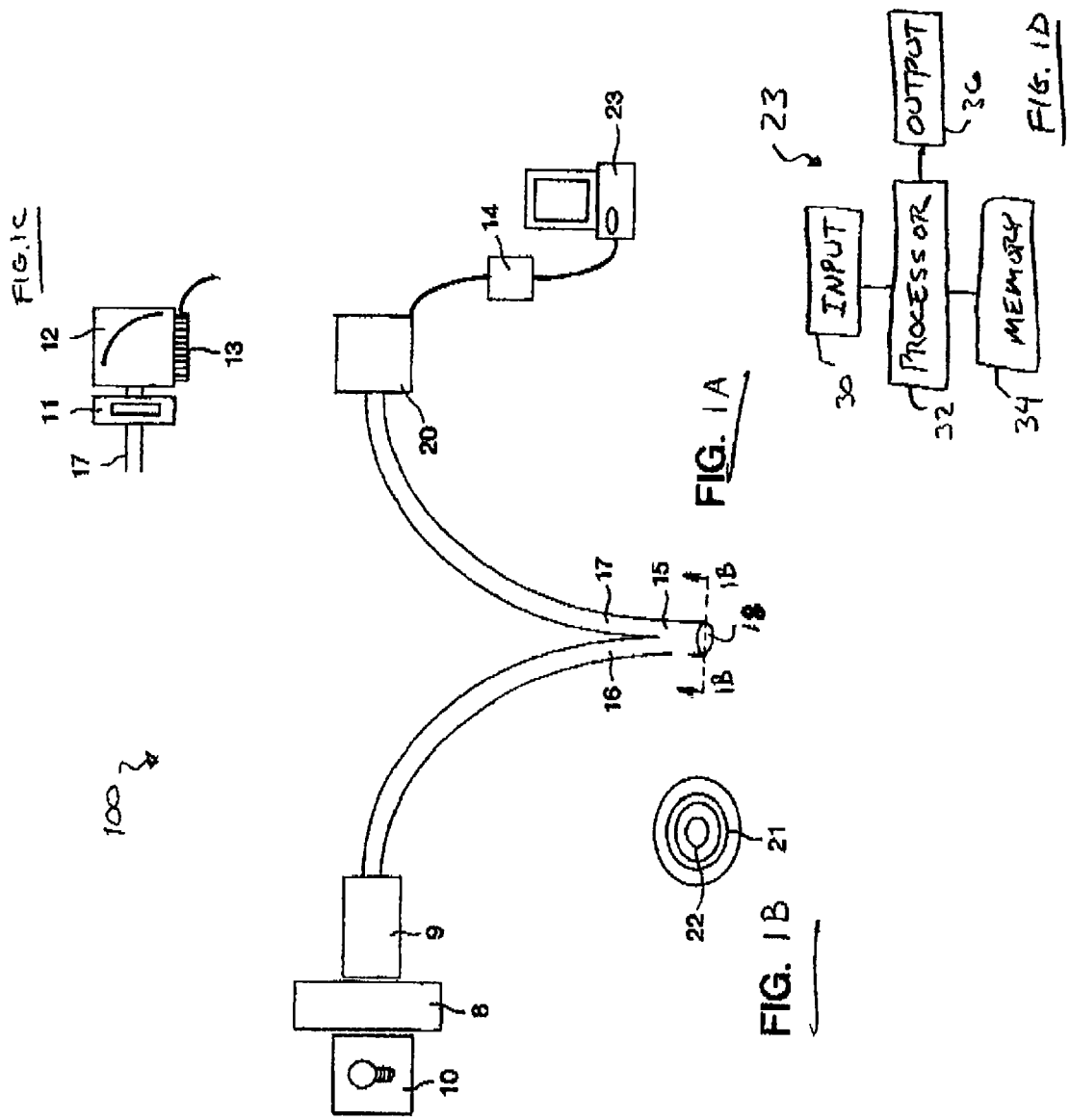

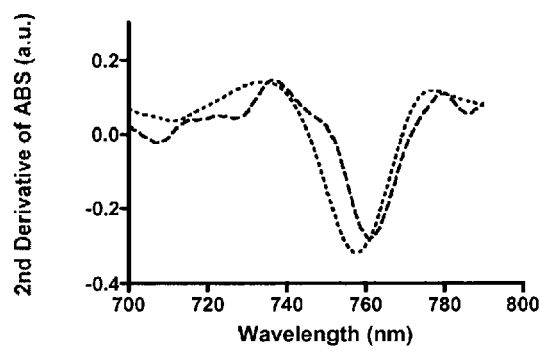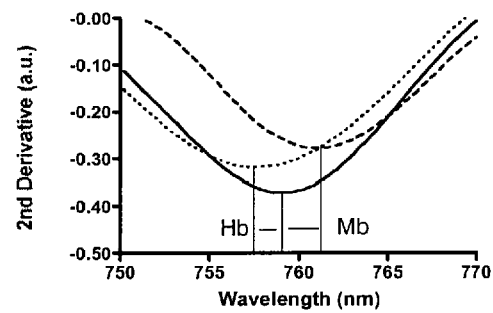
FIGURE 3A
FIGURE 3B

METHOD AND SYSTEM FOR DETERMINING THE CONTRIBUTION OF HEMOGLOBIN AND MYOGLOBIN TO IN VIVO OPTICAL SPECTRA

STATEMENT OF GOVERNMENT RIGHTS

The invention was made with Government support under Contract or Grant No. AR41928 awarded by the National Institutes of Health. The Government has certain rights in this invention.

TECHNICAL FIELD

This document pertains generally to optical spectra, and more particularly, but not by way of limitation, to a method and system for analysis of the relative contributions of hemoglobin (Hb) and myoglobin (Mb) to in vivo optical spectra.

BACKGROUND

Optical spectroscopy is emerging as an important modality for assessment of the biologic state of living tissues. Determination of the concentration of hemoglobin in biologic tissue has importance in determining blood flow, and in determination of the oxygen availability to cells within tissues, among other things. Variation in the optical scattering properties of tissue results in an unknown optical path length and makes quantifying chromophores in biological tissues difficult. Methods for accounting for the scattering coefficient directly, such as time-resolved or phase modulated spectroscopy, or indirectly, such as the use of the spectral absorption of water as an internal standard, are problematic in that they assume a constant scattering coefficient and rely on changes in the total heme chromophore signal (Hb+Mb) to determine changes in muscle perfusion, but provide little information on the resting conditions. The inability to distinguish the Hb and Mb signals means that the contributions of the intracellular (Mb) and vascular (Hb) compartments cannot be separated using traditional methods of analysis of optical spectra.

BRIEF DESCRIPTION OF THE DRAWINGS

In the drawings, which are not necessarily drawn to scale, like numerals describe substantially similar components throughout the several views. Like numerals having different letter suffixes represent different instances of substantially similar components. The drawings illustrate generally, by way of example, but not by way of limitation, various embodiments discussed in the present document.

FIGS. 1A, 1B, 1C, and 1D illustrate elements of an exemplary optical measurement system.

FIG. 3A illustrates the difference in the second derivative optical spectra between deoxy-Hb and deoxy-Mb around 760 nm.

FIG. 3B illustrates second derivative spectra showing the among deoxy-Hb, deoxy-Mb, and a complex in vivo spectrum around 760 nm.

DETAILED DESCRIPTION

Figure 2A:
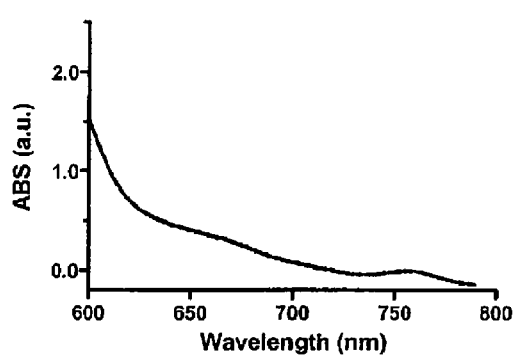
FIG. 2A illustrates an example of in vivo optical spectrum from a mouse hind limb.

The following detailed description includes references to the accompanying drawings, which form a part of the detailed description. The drawings show, by way of illustration, specific embodiments in which the present subject matter may be practiced. These embodiments, which are also referred to herein as "examples," are described in enough detail to enable those skilled in the art to practice the present subject matter. The embodiments may be combined, other embodiments may be utilized, or structural, logical and electrical changes may be made without departing from the scope of the present subject matter. The following detailed description is, therefore, not to be taken in a limiting sense, and the scope of the present subject matter is defined by the appended claims and their equivalents.

In this document, the terms "a" or "an" are used, as is common in patent documents, to include one or more than one. In this document, the term "or" is used to refer to a nonexclusive or, unless otherwise indicated. Furthermore, all publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

The present subject matter relates to quantitative analysis of the contributions of hemoglobin and myoglobin to optical spectra taken through intact biological tissue. Analysis of the optical spectra can be used to determine the contributions of Hb and Mtb to the optical signal. In an exemplary embodiment, the Hb/Mb ratio reflects relative concentrations in intact mouse skeletal muscle. In addition, quantitative Hb concentration can be determined, when a known or assumed value of myoglobin concentration is used.

For one example, the peak of the deoxygenated tissue at around 760 nm is used to determine the ratio of Hb to Mb contributing to the optical signal. The wavelength of this peak is a linear function of the percent contribution of Hb to the optical spectra. This linear relationship can be used to predict the Hb content of, for example, mouse hind limb skeletal muscle using in vivo optical spectra. In one example, the Hb/Mb ratio was determined in the ischemic leg from the optical spectra. Mb concentration, from literature values, as measured in tissue homogenates, or measured using other non-invasive modalities (e.g. magnetic resonance), can be used to calculate Hb concentration from the in vivo Hb/Mb ratio. In a similar manner, other absorbance peaks can be used to determine the ratio between Hb and Mb. In particular, the alpha and beta peaks of the oxygenated forms of Hb and Mb can be analyzed. Differences between the Soret peaks in the UV spectral region can also be used for this analysis.

The relationship between deoxy-peak position and Hb/Mb ratio is independent of the scattering coefficient and therefore does not require knowledge of the scattering properties or photon path length through the tissue. Analysis of optical spectra is used to measure the contribution of Hb and Mb to optical spectra. The analysis, in combination with known Mb concentrations, yields a non-invasive measure of the Hb content in skeletal muscle.

Optical spectroscopy (OS) can be used to monitor tissue blood flow and muscle oxygenation. Restricted skeletal muscle blood flow and poor muscle oxygenation are characteristics of a variety of pathological conditions including diabetes, chronic obstructive pulmonary disease (COPD), chronic heart failure (CHF) and is a key factor contributing to exercise intolerance in disease states. Optical spectroscopy takes advantage of the differences in the optical spectra between oxygenated and deoxygenated Hb and Mb to follow changes in muscle oxygenation by measuring the optical absorbance at several wavelengths.

Interpretation of these optical spectroscopy data is limited by the unknown contributions of Hb and Mb to the optical spectra. If Hb is the major component of the signal, the optical data provides information primarily on vascular oxygenation and if Mb is the major contributor, then the optical data provides a window into intracellular oxygenation.

The present subject matter allows quantification of the relative importance of Hb and Mb signals in, for example, skeletal muscle and provides an analysis tool to separate these signals despite their similar spectral properties. The present subject matter can also be used in cardiac muscle measurements from the heart.

The present subject matter takes advantage of the small (~4 nm) spectral shift between the peaks of deoxy-Hb and Mb in the near-infrared spectral region. A comparison of the position of the peak around 760 nm from deoxygenated tissue with those from pure deoxy-Hb and deoxy-Mb solutions allows determination of the Hb/Mb ratio in the tissue. The present subject matter determines the contribution of Hb and Mb to in vivo optical spectra independent of optical scattering. The present subject matter determines the contributions using peak position rather than peak amplitude or shape. This approach can be used when fully oxygenated or deoxygenated Hb and Mb are present, or when the saturation of both Hb and Mb are known. In these instances, analysis can be performed in the visible or UV wavelength region using, for example, the Soret peaks or the alpha and beta peaks of the oxygenated forms of Hb and Mb. Also, the deoxygenated peaks of Hb and Mb in the visible region can be used, when deoxygenated muscle is analyzed.

Exemplary Materials and Methods

In one example, optical analysis of Hb and Mb content was performed for hind limbs of four female Swiss-Webster mice. The mice were anesthetized with an intraperitoneal dose of 0.65 mg tribromoethanol diluted in sterile saline/g body weight. The hair was removed from the hind limbs using a commercial hair removal cream (Neet®, Premier Inc., Greenwich, Conn.) to improve the penetration of light through the leg. The mouse was positioned on its side and the experimental leg was pulled through a cuff used to induce ischemia and then secured in place with laboratory tape. The leg was positioned between two fiber optic bundles; one from the light source and one going to the detector such that the light traveled through the leg distal to the knee. The experimental protocol included a short baseline resting period followed by 10 minutes of ischemia induced by inflating the cuff around the upper leg to 200 mm Hg (26.7 kPa). Following 10 minutes of ischemia, a short piece of surgical umbilical cord was tied around the leg to prevent a change in the blood content of the leg. The animal was then repositioned and the protocol was repeated on the other leg. The legs were then removed and immediately frozen in liquid nitrogen. Throughout the experiment a surgical plane of anesthesia was maintained based on the lack of the toe pinch reflex.

Optical transmission spectra were acquired using 3.18 mm diameter fiber optic bundles to carry illuminating light from the source and transmitted light to the detector. Illumination from a 250 W quartz-tungsten-halogen light source (Roper Scientific, part no. TS-428) set to 60% maximum power was passed through an infrared filter to reduce tissue heating before entering the fiber bundles. Transmitted light was detected using an Inspectrum 300 mm spectrograph (Roper Scientific, part no. INS-300-124F) equipped with a front illuminated 124×1024 peltier cooled CCD chip and mechanical shutter. A 300 g/mm grating provided 0.25 nm pixel to pixel spectral resolution. Absorbance data was collected with a slit width of 250 μm and 100 μs exposure time at 1-sec intervals with Spectrasense v4.0 software (Roper Scientific Acton Research, Acton, Mass.).

FIG. 1A illustrates exemplary fiber optic probe system 100 for non-invasive measurement of contributions that Hb and Mb make to in vivo optical spectra. The optical spectra can include transmission spectra, reflectance spectra or both transmission and reflectance spectra.

System 100 includes detector 20 and fiber-optic reflectance probe 15. Light from source 10 is conveyed by probe 15 to detector 20. In one example, detector 20 includes a fiber-optic spectrophotometer having a CCD detector or photodiode array. Probe 15 includes a bifurcated fiber optic element having an input bundle 16 (illuminating fibers) and output bundle 17 (detector fibers). In one example, bundle 16 and bundle 17 include a plurality of optically conductive fibers (such as glass fibers).

Probe 15 includes distal end 18. FIG. 1B illustrates a view of distal end 18 in which the two fiber bundles are formed into a bull's eye, or concentric, configuration with the input bundle 16 forming outer ring 21 and output bundle 17 at center 22. Other probe configurations can be used, including transmission of light through a tissue sample.

The distance between input fibers 21 and output fibers 22 is adjustable and is selected to determine the depth of tissue sampling which is also a function of the wavelength illuminating a sample. Generally, the sampling depth increases with increased spacing between the illuminating and detector fibers. The distance is also adjusted to maintain useful signal level returned to the detector fibers. The signal level generally decreases with increased spacing.

Probe 15 is useful in reflectance measurements, in order to assure that a discrete minimal optical path length through tissue is obtained and to avoid mere sampling of the most superficial elements of tissue. In one example, the source to detector separation is roughly twice the average depth of penetration of light into tissue, and thus setting the spacing between the two sets of fibers between about 1 mm to about 3 mm provides an average penetration of about 0.5 mm to about 1.5 mm, respectively. In addition, the use of a contacting probe reduces the surface specular reflection of light contributing to the detected signal. In operation, light from source 10 is delivered to a sample via outer ring 21 and light reflected from the sample is received by center 22 and conducted to detector 20. For measurements in the visible wavelength region, the fiber spacing can be about 1 mm, corresponding to an average sampling depth of approximately 0.4 mm (with a maximum depth of about 1.8 mm). For measurement in the near infra-red wavelength region, the fiber spacing can be about 3 mm, corresponding to an average sampling depth of about 1.5 mm. Other spacing dimensions and sampling depths are also contemplated. In one example, source 10 includes a pulsed light source to allow for gated data collection. In one example, source 10 includes a shuttered light source where the shutter is opened and closed around spectral acquisition. Selective data collection can be triggered or timed by a selected event, for example a physiological event. In various examples, data collection is synchronized or triggered with in in vivo measurements by the cardiac cycle, the respiratory cycle or both. In the example illustrated, system 100 includes filter 9. Filter 9 can include a water filter and is configured to decrease heating of the illuminated tissue sample. In the example illustrated, shutter 8 includes a mechanical or electro-optical light shutter to provide pulsed sample illumination.

System 100 can operate using visible light, near infrared (NIR) and electromagnetic energy in other ranges including ultraviolet light.

The reflectance signal is conveyed to detector 20. FIG. 1C illustrates exemplary detector 20 having slit 11 and diffraction grating 12 coupled to photodiode array or CCD detector 13, thus providing photodiode or CCD detection as a function of wavelength. The signal from detector 13, in the example illustrated, is read into analog-to-digital (A/D) converter 14. The resulting digitized data is stored in a memory of computer system 23 and is used for data analysis.

Computer system 23 is illustrated in greater detail at FIG. 1D. Input 30 includes a user-operable keyboard for manual entry of data, an input interface for coupling to an A/D converter or an interface to another signal source (wired or wireless). Input 30 is coupled to processor 32. Processor 32 is configured to execute instructions stored on memory 34 or received from input 30. Memory 34, in various examples, includes a volatile or non-volatile memory or storage device. Output 36 is coupled to processor 32 and, in various examples, includes a display, a printer, a wireless transmitter or transceiver or other output device configured to render an output based on the generated results.

In one example, computer system 23 can be viewed as a data receiver for receiving spectral data. A memory device, such as memory 34, of computer system 23 stores the data and a calibration spectra and a processor, such as processor 32, is configured to execute instructions to generate Hb/Mb ratio or hemoglobin concentration information using the measured spectra.

Detector 20, in one example, includes a spectrometer. Various types of spectrometers are contemplated including those having a stationary prism and stationary sensor array, a swept prism and a stationary sensor, and a stationary prism and a swept sensor. Detectors may be photodiode arrays, charged coupled devices (CCDs) or other types of detectors.

Probe 15, in one example, includes fiber optic bundles held in a desired configuration to achieve a desired spacing between illuminating and detector fibers. For example, the fiber bundles can be inserted into an appropriately machined holder. The holder can be made of any inert, preferably non-toxic material, for example, metal, polymer material or plastic. End 18 of probe 15 is polished to obtain a highly smoothed surface, in which the fiber ends are substantially perpendicular to the plane of the distal end face. In one example, a mirrored surface is in contact with the tissue rather than the fibers themselves. In one example, other structures or methods are used to receive optical data.

In one example, probe 15 is configured for human use and has no metallic parts to ensure that patients are electrically isolated from the spectrometer and can withstand repeated sterilizations in an autoclave.

FIG. 1B illustrates a concentric bull's eye arrangement of fibers. Alternate arrangements of illuminating and detector fibers at end 18 can be used. For example, a checkerboard arrangement of fibers, which maintains the desired optimal spacing between illuminating and detector fibers, can be employed. In one example, end 18 is configured with spaced strips of illuminating and detector fibers. Either transmission, in which distinct fiber optic bundles carry optical signal from the source and to the detector, and reflectance configurations can be used to acquire optical spectra.

In use, end 18 is placed or held in contact with the tissue sample or at a selected position in contact with an organ, for example in contact with cardiac muscle, skeletal muscle or skin. Contact with the sample can be continuous, intermittent or periodic. Sample measurement can be continuous, intermittent or periodic.

The method and device of the present subject matter can be employed for non-invasive measurement of Hb and Mb. As used herein the term non-invasive includes measurements that inflict no damage to biological tissue, yet which may require contact with biological tissue. Methods also include those that are invasive or minimally invasive of tissue, for example those that may employ a trans-illumination needle probe that is inserted into the muscle tissue. An exemplary needle probe configuration includes two needle probes which are spaced apart, one of which carries the illuminating fiber and the other of which carries the detector fiber. A transmission spectrum of the tissue between the two needle ends can be obtained with such a probe. One example includes both transmitting and detecting fibers in the same needle probe. In various examples, the present subject matter includes contacting or non-contacting probes. A variety of methods for contacting the fiber optic probe with a tissue sample (either in vivo or in vitro) can be employed. For example, cardiac muscle measurements can be obtained by direct contact with the heart muscle during surgery or indirectly by minimally invasive techniques, for example, via catheter insertion of the probe or via insertion of the probe by trans-esophageal methods as used in trans-esophageal echocardiography. In one example, a trans-illumination implementation uses two inserted probes (one illuminating and one detecting) to collect transmission spectra of tissue between the probes. Transmission spectra of skeletal muscle may, in some cases, be obtained through the skin.

In one example, system 100 includes a broadband white light source to illuminate muscle tissue and detects color (spectral) changes in the reflected light returned to a spectrometer.

Exposure times are typically 50-200 ms. In one example, the reflected light has penetrated through a mouse hindlimb muscle (approximately 6 mm) and is a true tissue measurement (not just a surface measurement).

In one example, probe 15 functions as an optical receiver for receiving an optical signal from in vivo tissue. Probe 15 provides a signal based on light source 10. In one example, light source 10 includes a light emitting diode (LED). In one example, detector 20 includes a spectrometer having at least one of a photodetector, a photomultiplier tube, a photodiode, and a charge-coupled device (CCD). In one example, a QTH (quartz, tungsten-halogen) lamp is used. Detector 20 generates a reflectance spectrum for a plurality of wavelengths. Memory 34 of computer system 23 stores calibration spectra and processor 32 executes instructions to generate data using the calibration spectra and the absorption spectrum. Portions of system 100 can be disposed within a housing having a battery (or other power supply).

In one example, reference and calibration spectra were acquired using a 6 mm path length glass cuvette. Absorbance data were collected from the mouse leg using a 1% Intralipid (Baxter Scientific) (v/v) solution as reference. The calibration set was created to mimic conditions in vivo where there was a constant Mb concentration with varying levels of Hb contributing to the spectra. The calibration set included solutions containing 0, 30, 60, 90, and 100% Hb contribution to the total heme signal with 43 µM Mb in each solution (except for 100% Hb). Calibration sets were prepared with 0.5, 1, 1.5, and 2% scattering solutions. Fifty spectra were collected for each calibration solution. The last 50 spectra collected during ischemia in the mouse leg were used to determine the Hb/Mb ratio in vivo.

Data analyses were performed with MATLAB scripts. Analysis was performed on the second derivative of the absorbance spectra to remove baseline offsets for easier visual examination of the data. A cubic spline function was used to fit the data and fill in 100 points between each collected data point. The position of the deoxy peak (minimum in the second derivative) around 760 nm was determined for each spectrum and the mean of the 50 spectra was used to determine the peak position for each calibration and experimental group. These values were used to compute the Hb/Mb ratio from the experimental spectra.

Hb and Mb concentrations were quantified from SDS-PAGE (sodium dodecyl sulphate, polyacrylamide gel electrophoresis) gels. These values were determined in triplicate for each leg. The Mb value from this biochemical analysis was used in combination with the Hb/Mb ratio from the optical analysis to calculate the Hb concentration in the mouse muscle.

Figure 2B:
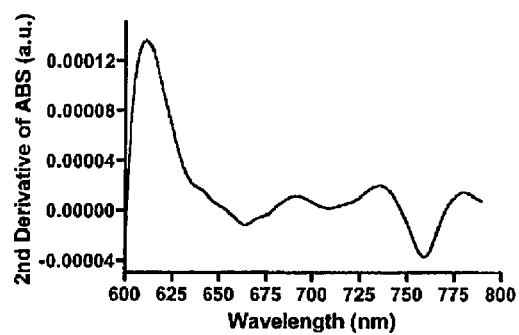
FIG. 2B illustrates a second derivative of the spectrum with respect to wavelength shown in FIG. 2A.

The present subject matter considers the spectral shift of the deoxy-Hb spectrum relative to that of deoxy-Mb. FIG. 2A illustrates an example of in vivo optical spectrum from a mouse hind limb. FIG. 2B illustrates a second derivative of the spectrum shown in FIG. 2A. Taking the second derivative removes baseline offsets and sharpens the spectral features. In one example, the peak of the deoxygenated proteins around 760 nm is used for analysis.

The difference between the second derivative spectra of pure deoxy-Hb and deoxy-Mb is shown in FIG. 3A. The position of the 760 nm peak of a complex in vivo spectrum between those of pure deoxy-Hb and deoxy-Mb solutions is illustrated in FIG. 3B. FIG. 3 illustrates second derivative spectra showing the difference between deoxy-Hb, deoxy-Mb, and a complex in vivo spectrum around 760 nm.

In FIG. 3B the solid line represents the in vivo spectrum taken at the end of ischemia. This figure demonstrates that the peak minimum of the $2^{nd}$ derivative of the in vivo spectrum falls between the peaks (minima of the $2^{nd}$ derivative) of the spectra from the deoxygenated Hb and Mb solutions.

Figure 4:
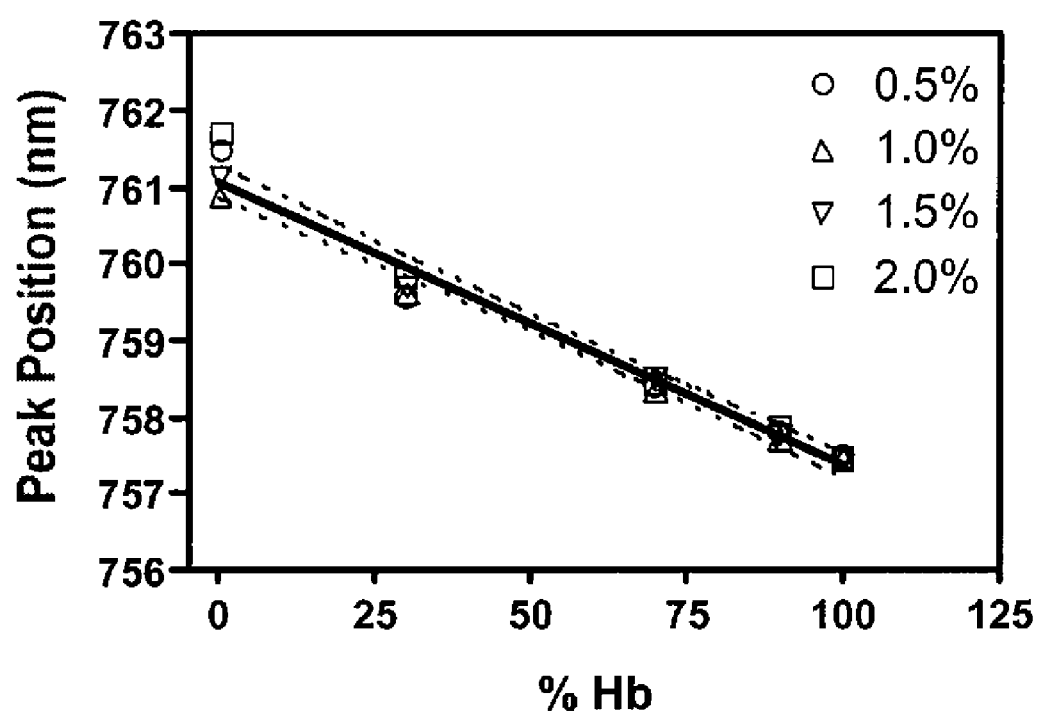
FIG. 4 illustrates a relationship between percentage Hb and peak position that is independent of scatterer concentration.

The position of the experimental 760 nm peak between the extremes set by the Hb and Mb solutions is dependent on the ratio of Hb and Mb contributing to the spectra in the fully deoxygenated tissue. This relationship is linear over the entire range of Hb contributions (0-100%) as demonstrated by the plot of a calibration set in FIG. 4. FIG. 4 illustrates a relationship between percentage Hb and peak position that is independent of scatterer concentration.

The relationship between peak position and % Hb was tested over a range of scattering coefficients (0.5-2.0% Intralipid) to bracket the range of optical scattering properties in muscle tissue in vivo. The slopes and y-intercepts calculated for each scatterer concentration were not significantly different (ANCOVA, $P=0.57$ and $P=0.61$, respectively). The regression illustrated in FIG. 4 represents all four data sets pooled. This regression was used to calculate in vivo Hb/Mb from in vivo optical spectra.

The concentration of Hb in the mouse hind limbs was calculated from the Hb/Mb ratio determined from optical spectra and Mb concentration measured using gel electrophoresis.

Analysis of in vivo optical spectra can be used to quantify the contributions of Hb and Mb to optical spectra of biological tissues. Because Hb and Mb are confined to distinct tissue compartments, their saturation states yield different information on tissue oxygenation—Hb reflects vascular oxygenation, while Mb reflects intracellular oxygenation. In addition, oxygen affinity of Mb is also approximately 10× greater than for Hb.

Given these differences, the ability to quantitatively interpret optical data from intact tissue is severely limited by the lack of knowledge of the contributions of each to the signal. With a calibration set and analysis of the deoxy-Hb/deoxy-Mb peak position, the present subject matter determines the Hb/Mb ratio for different conditions throughout an experiment.

Analysis indicates that in resting mouse hind limb 80-90% of the heme optical signal is due to Hb absorbance. These results are consistent with findings indicating that small mammals like the mouse should have low Mb and high Hb concentrations in their skeletal muscles. It is also reasonable to expect that the percent contribution of Hb in larger mammals is lower than for a mouse.

The present subject matter quantifies the contributions that Hb and Mb make to in vivo optical spectra. In addition, the present subject matter is independent of optical scattering properties of the tissue because it uses the position of a spectral peak, for example the position of the deoxy Hb and Mb peaks in the near-infrared region (~760 nm).

The present subject matter uses optical wavelengths in intact tissue to quantify hemoglobin concentration in vivo.

The ability to quantify Hb and Mb content in vivo now allows for a non-invasive measurement of tissue $O_2$ consumption. Previous methods independently measure Hb and Mb saturations in vivo in skeletal muscle to quantify tissue oxygen consumption rates. Quantifying the rates of $O_2$ consumption from changes in tissue $O_2$ stores requires that the concentrations of Hb and Mb in the tissue as well as the saturations are known. Therefore, earlier methods are limited to use in animal models where the tissue could be frozen following the in vivo experiments and Hb and Mb concentrations could be measured from muscle homogenates. The ability to measure the Hb/Mb ratio with the present subject matter, combined with magnetic resonance quantification of Mb, or estimates of Mb concentration from literature values, now provides a fully non-invasive approach to measuring the rate of oxygen consumption of human skeletal muscle.

Myoglobin concentrations in human tissue vary much less between individuals and with disease states than do hemoglobin concentrations. The ability to assume a constant myoglobin concentration allows for clinical measurement of Hb concentration from Hb/Mb ratios. Many diseases, like diabetes, chronic heart failure, and chronic obstructive pulmonary disease are characterized by impairment of peripheral blood flow. The ability to quantify Hb content in vivo in the clinic is expected to allow earlier diagnosis of problems in peripheral circulation and provide the opportunity to start interventions before clinical symptoms are present.

Figure 5:
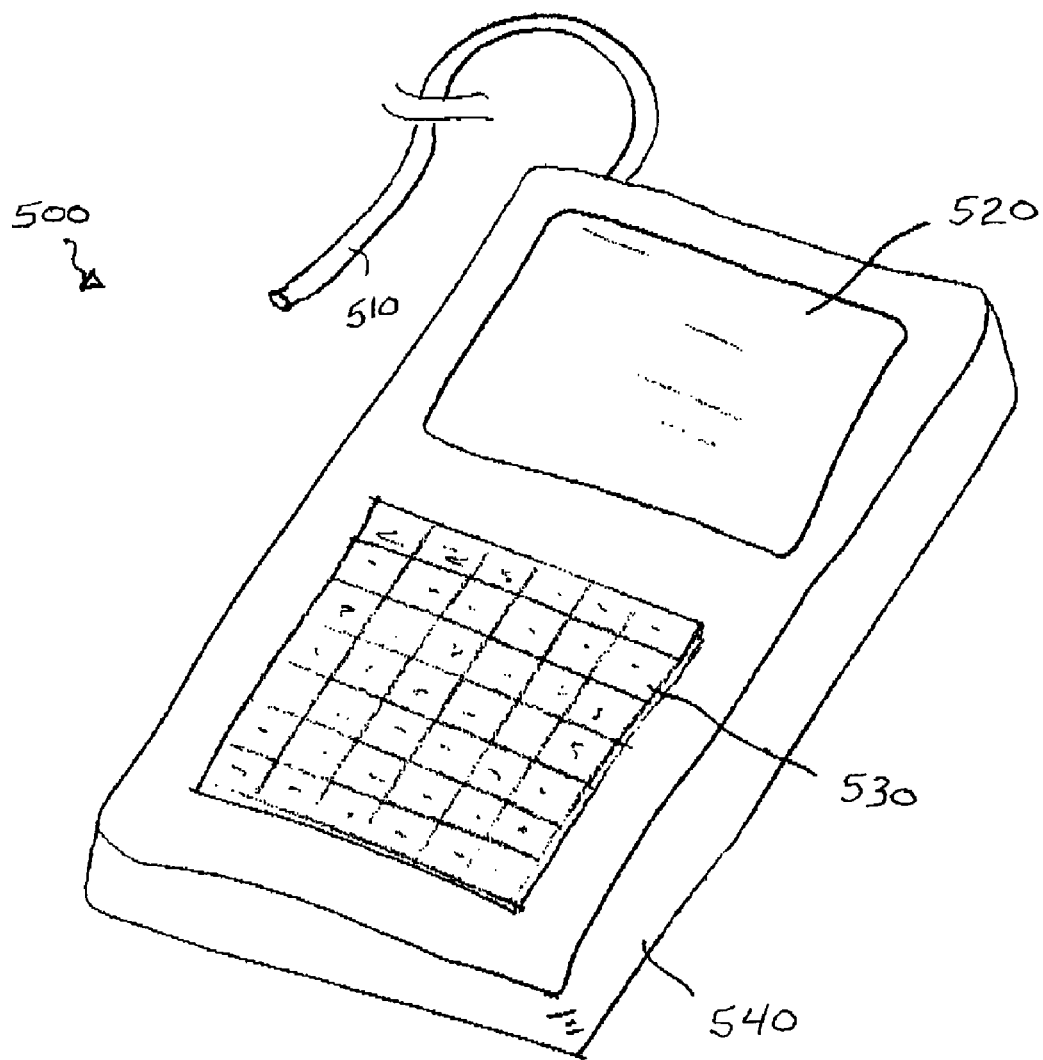
FIG. 5 illustrates a portable device.

FIG. 5 illustrates exemplary handheld device 500 suitable for clinical use. Device 500 includes probe 510 having an optical fiber coupled to circuitry (not shown) disposed within housing 540. The circuitry includes a processor and a memory such as illustrated in FIG. 1D. The memory stores the calibration spectra, the measured data and executable instructions for implementation of an algorithm by the processor. Results of the analysis are presented on display 520. A user can control the operation of device 500 using keyboard 530 disposed on a surface of housing 540. Results generated by device 500 can be stored in memory (internal or external to housing 540), displayed on display 520, or printed (using an external printer) or transmitted wirelessly. In one example, housing 540 is portable and includes at least a portion of computer system 23 (FIG. 1D) disposed therein.

Probe 510, in one example, includes a bifurcated fiber optic element. A light source and a detector are disposed within housing 540 and coupled to probe 510. Device 500 can be tailored to generate data based on transcutaneous illumination of tissue such as a heart or leg muscle. In one example, probe 510 is inserted into a muscle or other tissue.

A memory of device 500 stores a library or database for comparison or interpolation. In one example, the database includes data suitable for use with children, adults and people of different races or ethnicity. Device 500 is configured to be insensitive to stray light or skin pigmentation.

Device 500 can be used for quantitative analysis of the contributions of hemoglobin and myoglobin to optical spectra taken through intact biological tissue.

The present subject matter includes a method for optical determination of hemoglobin concentration, which provides a quantitative measure of blood supply in tissue.

Alternative Examples

Figure 6:
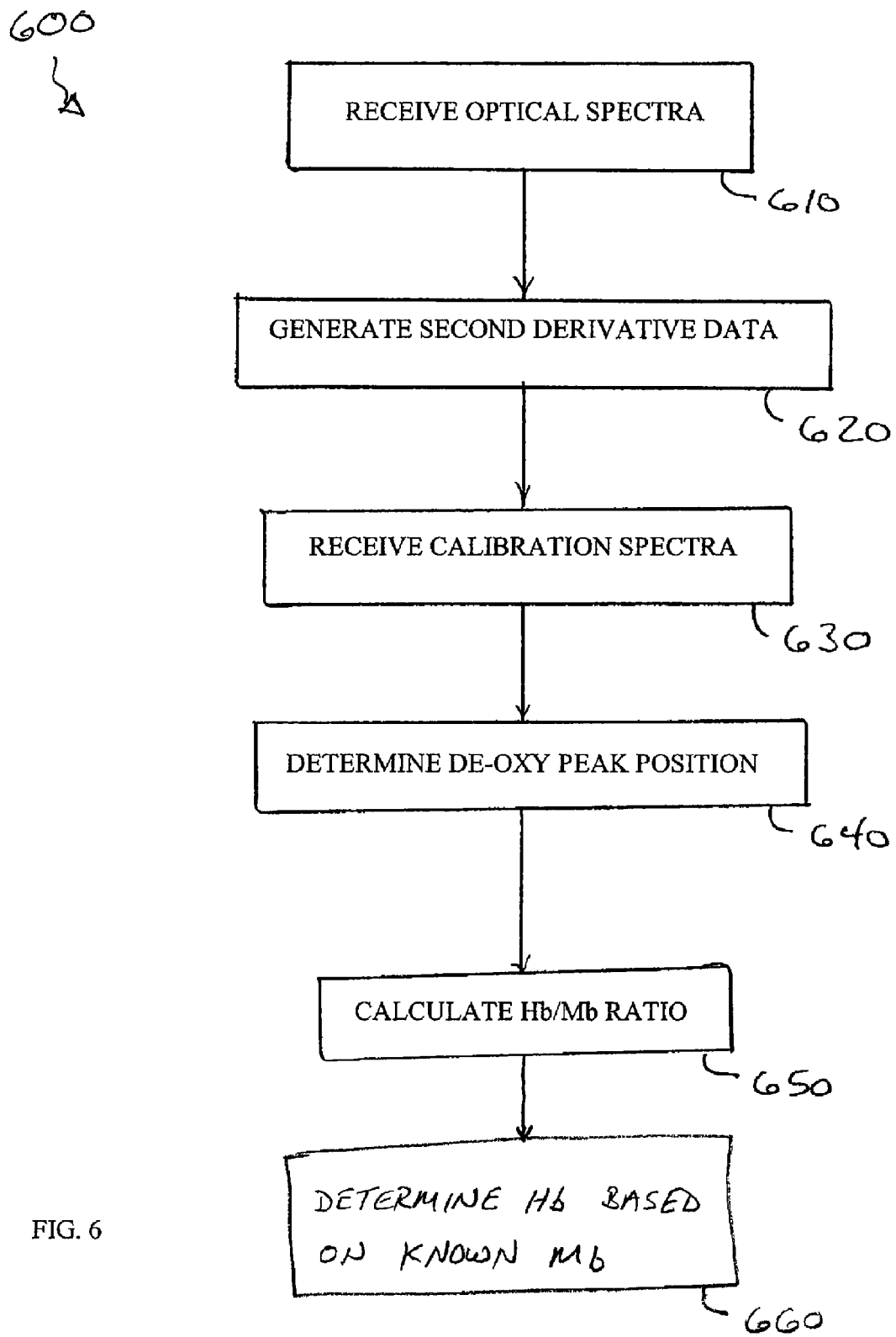
FIG. 6 illustrates a method according to the present subject matter.

FIG. 6 illustrates method 600 according to one example of the present subject matter. At 610 of method 600, an optical spectra is received. The spectra can be a reflectance spectra, a transmission spectra or other data corresponding to spectra for tissue. At 620, a second derivative is generated for the optical spectra. At 630, calibration spectra is received or accessed. In one example, the calibration spectra includes data corresponding to a plurality of wavelengths. At 640, a position of a deoxy peak is calculated. In various examples, this includes a calculation as to a deoxy peak for Hb and a deoxy peak for Mb. At 650, a ratio is calculated for Hb/Mb. At 660, the absolute Hb concentration is calculated using the Hb/Mb from step 650 and a known Mb concentrations determined from literature values or measured by other non-invasive approaches such as magnetic resonance. At 660, the hemoglobin concentration is determined as a product of the Hb/Mb ratio and known myoglobin concentration.

The optical spectrum received from a tissue can include a range of wavelengths in the UV, visible or near-infrared or other electromagnetic regions. The optical spectra can be received in the form of stored digital or analog data. In one example, the optical signal is received using a fiber optic element.

At 620, other functions can be used to remove baseline offsets or other artifacts. In one example, the data is used without generating a second derivative. Other processing can also be included, including a smoothing function. The data analysis and processing can be performed by one or more processors executing instructions.

It is to be understood that the above description is intended to be illustrative, and not restrictive. For example, the above-described embodiments (and/or aspects thereof) may be used in combination with each other. Many other embodiments will be apparent to those of skill in the art upon reviewing the above description. The scope of the subject matter should, therefore, be determined with reference to the appended claims, along with the full scope of equivalents to which such claims are entitled. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The Abstract of the Disclosure is provided to comply with 37 C.F.R. §1.72(b), requiring an abstract that will allow the reader to quickly ascertain the nature of the technical disclosure. It is submitted with the understanding that it will not be used to interpret or limit the scope or meaning of the claims. In addition, in the foregoing Detailed Description, various features may be grouped together to streamline the disclosure. This method of disclosure is not to be interpreted as reflecting an intention that the claimed embodiments require more features than are expressly recited in each claim. Rather, as the following claims reflect, inventive subject matter may lie in less than all features of a single disclosed embodiment. Thus the following claims are hereby incorporated into the Detailed Description, with each claim standing on its own as a separate embodiment.

What is claimed is:

1. A method comprising: detecting an optical spectra from in vivo tissue; receiving a calibration spectra; determining a peak position based on the optical spectra between a spectral peak for hemoglobin and a spectral peak for myoglobin based on the calibration spectra; and calculating a ratio of Hb and Mb in the tissue based on the peak position.

2. The method of claim 1 wherein the spectral peak for hemoglobin corresponds to peak deoxy-hemoglobin and the spectral peak for myoglobin corresponds to peak deoxy-myoglobin.

3. The method of claim 1 wherein the spectral peak for hemoglobin corresponds to peak oxy-hemoglobin and the spectral peak for myoglobin corresponds to peak oxy-myoglobin.

4. The method of claim 1 further including:
   receiving a known concentration of myoglobin for the tissue; and
   calculating a concentration of hemoglobin based on the known concentration of myoglobin and the ratio.

5. The method of claim 1 wherein detecting the optical spectra includes detecting at least one of reflectance and transmission spectra.

6. The method of claim 1 further including calculating a second derivative of the optical spectra and wherein determining the peak position includes using the second derivative.

7. The method of claim 1 further including detecting a spectral shift.

8. The method of claim 1 wherein detecting the optical spectra includes detecting spectra in the near infrared or visible region.

9. A system comprising:
   a data receiver configured to receive data corresponding to optical spectra of in vivo tissue;
   a memory device configured to store the data and configured to store calibration spectra; and
   a processor coupled to the memory device and configured to execute instructions to determine a peak position in the data and generate a ratio of hemoglobin and myoglobin based on the peak position relative to a spectral peak for hemoglobin and a spectral peak for myoglobin based on the calibration spectra.

10. The system of claim 9 wherein the peak position corresponds to at least one of deoxy-myoglobin, deoxy-hemoglobin, oxy-myoglobin, and oxy-hemoglobin.

11. The system of claim 9 further including an output device coupled to the processor and configured to render an output based on the ratio.

12. The system of claim 11 wherein the output device includes at least one of a printer, a display, and a transmitter.

13. The system of claim 9 further including a portable housing and wherein at least one of the data receiver, memory device and the processor is disposed therein.

14. The system of claim 9 wherein the processor is configured to execute instructions to generate a quantitative measure of hemoglobin based on the ratio.

15. The system of claim 9 wherein the processor is configured to generate a second derivative of the spectra.

16. The system of claim 9 further including a spectrograph coupled to the data receiver.

17. The system of claim 9 wherein the processor is configured to generate the ratio based on a position of a spectral shift of the spectra.

18. A method comprising: detecting an optical spectra from intact biological tissue; determining a spectral shift in a peak position between a spectral peak for hemoglobin and a spectral peak for myoglobin in the optical spectra; and determining a ratio of hemoglobin and myoglobin in the tissue based on the spectral shift.

19. The method of claim 18 wherein detecting the optical spectra includes detecting optical spectra in a near infrared or visible region.

20. The method of claim 18 wherein determining the spectral shift in the peak position between the spectral peak for hemoglobin and the spectral peak for myoglobin in the optical spectra includes determining a peak corresponding to at least one of deoxy-myoglobin, deoxy-hemoglobin, oxy-myoglobin, and oxy-hemoglobin.

21. The method of claim 18 wherein determining the spectral shift in the peak position between the spectral peak for hemoglobin and the spectral peak for myoglobin in the optical spectra includes comparing the peak position to a peak position of a calibration set.

22. The method of claim 18 wherein detecting the optical spectra includes detecting at least one of reflectance spectra and transmission spectra.

* * * * *